(12) United States Patent
Rehbein

(10) Patent No.: US 11,596,734 B2
(45) Date of Patent: Mar. 7, 2023

(54) TRIGGER ARRANGEMENT FOR AN INFUSION DEVICE

(71) Applicant: SANOFI, Paris (FR)

(72) Inventor: Christian Rehbein, Budenheim (DE)

(73) Assignee: Sanofi, Paris (FR)

( * ) Notice: Subject to any disclaimer, the term of this patent is extended or adjusted under 35 U.S.C. 154(b) by 306 days.

(21) Appl. No.: 16/652,161

(22) PCT Filed: Oct. 9, 2018

(86) PCT No.: PCT/EP2018/077432
§ 371 (c)(1),
(2) Date: Mar. 30, 2020

(87) PCT Pub. No.: WO2019/072821
PCT Pub. Date: Apr. 18, 2019

(65) Prior Publication Data
US 2020/0246536 A1    Aug. 6, 2020

(30) Foreign Application Priority Data
Oct. 10, 2017   (EP) ..................................... 17306365

(51) Int. Cl.
*A61M 5/145*    (2006.01)

(52) U.S. Cl.
CPC ... *A61M 5/1452* (2013.01); *A61M 2205/3306* (2013.01); *A61M 2205/3317* (2013.01);
(Continued)

(58) Field of Classification Search
CPC ........ A61M 5/1452; A61M 2205/3306; A61M 2205/3317; A61M 2205/3569;
(Continued)

(56) References Cited

U.S. PATENT DOCUMENTS 6,492,978 B1 * 12/2002 Selig ................... G06F 3/04886
345/173
2007/0023045 A1 * 2/2007 Kwok ............... A61M 16/0057
128/204.23
(Continued)

FOREIGN PATENT DOCUMENTS

CA         2848274 A1 *   7/2007   ............ A61M 15/00
CN       101578607         11/2009
(Continued)

OTHER PUBLICATIONS

International Preliminary Report on Patentability in Application No. PCT/EP2018/077432, dated Apr. 14, 2020, 8 pages.
(Continued)

*Primary Examiner* — Nilay J Shah
(74) *Attorney, Agent, or Firm* — Fish & Richardson P.C.

(57) ABSTRACT

A trigger arrangement for an infusion device is disclosed, the trigger arrangement being configured to trigger a bolus injection of the infusion device and including: a body having an outside surface, a haptic structure arranged on the outside surface or integrated into the outside surface, wherein the haptic structure includes a first end section and a second end section and wherein the haptic structure includes a haptic track extending from the first end section to the second end section, a touch sensitive sensor arrangement extending along the haptic track and configured to detect a sliding motion of an object along the haptic track.

19 Claims, 4 Drawing Sheets

(52) U.S. Cl.
CPC .............. *A61M 2205/3569* (2013.01); *A61M 2205/505* (2013.01)

(58) Field of Classification Search
CPC ...... A61M 2205/505; A61M 2205/502; A61M 5/31566; A61M 2205/3561; A61M 2205/3553; G06F 3/0428; G06F 3/016; G06F 3/017
See application file for complete search history.

(56) References Cited

U.S. PATENT DOCUMENTS

| | | | |
|---|---|---|---|
| 2007/0186923 A1* | 8/2007 | Poutiatine | A61M 15/0083 128/200.14 |
| 2007/0257821 A1* | 11/2007 | Son | G06F 3/0446 341/22 |
| 2008/0246735 A1* | 10/2008 | Reynolds | G06F 3/016 345/173 |
| 2008/0316180 A1* | 12/2008 | Carmody | G06F 3/016 345/172 |
| 2011/0270219 A1 | 11/2011 | Friedli | |
| 2012/0212434 A1* | 8/2012 | Bluemler | G06F 3/04144 345/173 |
| 2013/0283196 A1 | 10/2013 | Farnan et al. | |
| 2013/0321297 A1 | 12/2013 | Li | |
| 2015/0363097 A1 | 12/2015 | Draper et al. | |
| 2016/0006856 A1* | 1/2016 | Bruno | H04M 1/72436 715/809 |
| 2016/0074573 A1 | 3/2016 | Kohlbrecher et al. | |
| 2016/0246935 A1* | 8/2016 | Cerny | A61N 1/0551 |
| 2017/0269716 A1 | 9/2017 | Schuster | |

FOREIGN PATENT DOCUMENTS

| | | |
|---|---|---|
| CN | 102819383 | 12/2012 |
| CN | 104615366 A * | 5/2015 |
| CN | 106687161 | 5/2017 |
| JP | 2013-218204 | 10/2013 |
| JP | 2017-500907 | 1/2017 |
| WO | WO 2008/070054 | 6/2008 |
| WO | WO 2012/155035 | 11/2012 |
| WO | WO 2014/118108 | 8/2014 |
| WO | WO 2015/066522 | 5/2015 |
| WO | WO-2016009202 A1 * | 1/2016 ............. A24F 15/01 |
| WO | WO 2016/040423 | 3/2016 |

OTHER PUBLICATIONS

International Search Report and Written Opinion in Application No. PCT/EP2018/077432, dated Nov. 9, 2018, 11 pages.
patents.google.com [online], "Machine Translation of CN104615366A: Gesture interactive method oriented to multiple devices," published May 13, 2015, retrieved Jul. 12, 2022, retrieved from URL <https://patents.google.com/patent/CN104615366A/en?oq=CN104615366a>, 11 pages.

* cited by examiner

TRIGGER ARRANGEMENT FOR AN INFUSION DEVICE

CROSS-REFERENCE TO RELATED APPLICATIONS

The present application is a national stage entry of International Patent Application No. PCT/EP2018/077432, filed on Oct. 9, 2018, and claims priority to Application No. EP 17306365.2, filed on Oct. 10, 2017, the disclosures of which are incorporated herein by reference.

TECHNICAL FIELD

The present disclosure relates to a trigger arrangement for an infusion device.

BACKGROUND

Drug delivery devices for setting and dispensing a single or multiple doses of a liquid medicament are known in the art. When configured as an injection device or as an infusion device they have a similar purpose as that of an ordinary syringe.

Injection devices, such as pen-type injectors, or infusion devices, such as patch pumps have to meet a number of user-specific requirements. For instance, a patient suffering chronic diseases, such like diabetes, may be physically infirm and may also have impaired vision. Suitable injection devices especially intended for home medication therefore need to be robust in construction and should be easy to use. Furthermore, manipulation and general handling of the device and its components should be intelligible and easily understandable.

Moreover, a dose setting as well as a dose dispensing procedure must be easy to operate and has to be unambiguous.

SUMMARY

The present disclosure relates to a trigger arrangement for an infusion device as well as to a remote control for an infusion device, to a respective infusion device and to a method of detecting a sliding motion of an object along a haptic track. The disclosure particularly relates to a trigger arrangement, to a remote control and to an infusion device that are configured to provide a bolus injection of a medicament. The trigger arrangement, the remote control and the infusion device are particularly configured to provide a blind bolus injection.

Compact drug delivery devices, e.g. portable infusion devices, such as patch pumps are carried around close to the body of a patient. Most of these portable infusion devices include a cartridge or a container filled with a liquid medicament that is expelled or withdrawn from the container by means of a drive mechanism. Delivery of the medicament to the patient is typically controlled by an electronic controller. The infusion device typically includes at least one or several actuation members in order to individually configure the rate, the amount and the time at which the medicament has to be delivered.

With portable infusion or injection devices it is possible to trigger a bolus injection, i.e., to prompt a delivery of a well-defined amount of the medicament upon a request of the user. For example with patients suffering diabetes, a bolus injection may need to be triggered as the patient intends or starts eating food or starts drinking caloric beverages. Since portable infusion or injection devices may be in direct contact with the skin of the patient, or since such devices may be worn under the clothes, it may be quite cumbersome for a patient to trigger a bolus injection since the portable delivery device is covered by the patient's clothes. In the everyday life of a patient, there may arise situations where a partial undressing for gaining access to the portable delivery device is rather inconvenient and unacceptable for the patient.

It is therefore desirable to provide a blind bolus injection functionality for such delivery devices, i.e., a function that enables one to trigger a bolus injection without requiring complete access to the delivery device or visual control of the delivery device.

Preferably, the blind bolus injection cannot be triggered inadvertently. Furthermore, starting or initiating blind bolus injections should be as easy as possible. The present disclosure provides an improved trigger arrangement for a delivery device, such as an infusion device, wherein the trigger arrangement is configured to trigger a bolus injection of the infusion device.

The trigger arrangement can impede or avoid inadvertent bolus injection and the trigger arrangement should be easy and intuitive in handling and operation to enable initiation of a bolus injection.

In one aspect, a trigger arrangement is provided for a drug delivery device, in particular for an infusion device. The trigger arrangement is configured to trigger a bolus injection of the infusion device. The trigger arrangement includes a body having an outside surface. The trigger arrangement further includes a haptic structure that is arranged on the outside surface or which haptic structure is integrated into the outside surface. The haptic structure includes a first end section and a second end section. The haptic structure further includes a haptic track. The haptic track extends from the first end section to the second end section. The trigger arrangement further includes a touch sensitive sensor arrangement extending along the haptic track, e.g. from the first end section of the haptic track to the second end section of the haptic track. The touch sensitive sensor arrangement is configured to detect a sliding motion of an object, e.g. a finger of a person, along the haptic track.

The haptic structure is haptically detectable. The location as well as the geometry of the haptic structure can be sensed and detected by way of touching. It is haptically perceptible. In particular, the haptic structure is palpable by a finger or by several fingers of a user. In this way a user or patient of the trigger arrangement and hence of the infusion device may trigger a bolus injection simply by haptically detecting the location of the haptic structure. It is not necessary to visually inspect the trigger arrangement of a remote control or of an infusion device, which may be carried underneath clothing. Furthermore the haptic structure includes a predefined geometry or elongation. It includes a haptic track extending from the first end section to the second end section. In order to avoid an inadvertent release of a bolus injection, an object, e.g., a finger of a patient slides along the entire or at least a portion of the haptic track.

The geometry of the haptic track may be selected such that an object can only slide intentionally along the haptic track, e.g., from the first end section to the second end section of the haptic structure. In this way an inadvertent activation of a bolus injection can be effectively avoided. With a given geometry of the haptic track any inadvertent touching of a portion of the haptic track will not lead to an activation of a bolus injection. This is because it is unlikely that the inadvertent touching exactly follows the geometric structure, the slope, and/or extension of the haptic track from the first end section of the haptic structure to the second end section of the haptic structure. In this way inadvertent triggering of a bolus injection can be effectively avoided.

If a patient or a user intends to release or to activate a bolus injection, the user simply has to palpate the haptic structure and slide along the entire haptic track from the first end section towards the second end section. A visual inspection or control of the trigger arrangement is not necessary. The user may simply operate the trigger arrangement while it is covered by the clothes of the user. A delivery device or a remote control for such delivery device and equipped with the trigger arrangement may be worn under the user's clothes. The bolus injection may be simply triggered by at least one of palpating, touching and sliding along the haptic structure of the trigger arrangement in a well-defined way.

The sliding motion of the object along the haptic track is detectable by the touch sensitive sensor arrangement. If a particular sliding pattern of the object is detected by the touch sensitive sensor arrangement, a bolus injection is triggered, typically by means of an electronic controller connected to the touch sensitive sensor arrangement and further connected or connectable to a drive mechanism of the infusion device.

According to an example, the haptic track includes a deepening in the outside surface of the body of the trigger arrangement. The body of the trigger arrangement may include or may form a housing of the trigger arrangement. A deepening of the outside surface is easily palpable or touchable, e.g., with one or several fingers of a user. The deepening may form or include a groove in the body of the trigger arrangement. The groove or the deepening may include a concave shaped cross-section that corresponds with the geometry of a fingertip. In this way a mutual contact surface between the fingertip and the deepening as well as between the fingertip and the touch sensitive sensor arrangement can be enlarged. A concave shaped groove is also economic for an intuitive handling of the trigger arrangement. The touch sensitive sensor arrangement extends along a bottom of the deepening or along the sidewall of the deepening. It may be integrated into the deepening and hence in the surface of the deepening. In some examples, the touch sensitive sensor arrangement may be located underneath the deepening, inside the body of the trigger arrangement The deepening may extend all along the haptic track, hence from the first end section of the haptic structure to the second end section of the haptic structure. Along the haptic track, the deepening may include a constant cross-section. Alternatively, it may include a varying depth or a varying cross-section as it extends from the first end section to the second end section of the haptic structure. In this way, the first end section and the second end section of the haptic structure, as well as portions of the haptic structure located between the first end section and the second end section, can be palpably distinguished. With a non-uniform cross-section of the deepening along the haptic track, the first end section can be palpably distinguished from the second end section. In this way the user is enabled to find at least one of the first and the second end sections of the haptic structure and to distinguish between the first and the second end sections of the haptic structure simply by way of touching and by means of haptic senses. In this way the user can identify the first end section of the haptic structure to start with a sliding motion along the haptic track. The depth or a cross-section of the deepening at or near the first end section of the haptic structure may be larger than a depth or cross-section of the deepening at or near the second end section of the haptic structure; or vice versa. In this way the first and the second end sections of the haptic structure become haptically discernible.

According to a further example, the haptic structure includes at least a first ridge protruding from the outside surface. The first ridge may extend along at least a portion of the haptic track.

The first ridge may extend all along the haptic track e.g., from the first end section to the second end section of the haptic structure. The first ridge may also form the haptic structure and may coincide with the haptic track. The touch sensitive sensor arrangement may be located inside the first ridge. As the user slides along the first ridge, a sliding motion can be detected by the touch sensitive sensor arrangement in order to release and to activate a bolus injection.

In another example, the at least first ridge protruding from the outside surface of the body may extend along the haptic track and may be located next to or adjacent to the haptic track. The first ridge may therefore provide a mechanical guiding structure for an object to slide along the haptic track and to slide along the touch sensitive sensor arrangement. The haptic track and/or the touch sensitive sensor arrangement may be flush mounted in or on the outside surface of the body of the trigger arrangement. By means of the at least first ridge extending along the haptic track and protruding from the outside surface, the haptic track located adjacent to the first ridge becomes haptically perceptible, i.e., palpable.

The at least first ridge may include a uniform and constant cross-section along the haptic track as it extends from the first end section to the second end section of the haptic structure. It is also conceivable, that the at least first ridge includes a non-uniform and varying cross-section along the haptic track. In this way the first end section and the second end section of the haptic structure and hence the haptic track becomes distinguishable for a user when touching the haptic structure and using his haptic senses. A protrusion of the first ridge at or near the first end section of the haptic structure may be larger than a protrusion of the first ridge at or near the second end section of the haptic structure; or vice versa. In this way the first and the second end sections of the haptic structure become haptically discernible.

According to another example, the haptic structure includes at least a second ridge protruding from the outside surface of the body. The second ridge extends parallel to the first ridge. The haptic track is located or extends between the first ridge and the second ridge. The haptically discernible haptic track becomes haptically discernible by means of the first ridge and by means of the second ridge. Both the first ridge and the second ridge are located at such a distance with respect to each other, that an object, e.g., a fingertip of a user, is insertable into an intermediate space between the first ridge and the second ridge. The outside surface of the body located between the first ridge and the second ridge and hence a portion of the outside surface being laterally confined by the first ridge and by the second ridge is typically provided with the touch sensitive sensor arrangement. The touch sensitive sensor arrangement is configured to detect a sliding motion of an object, e.g., of a finger of a user when sliding along the haptic track while being guided by the first and the second ridges.

Typically, the first ridge and the second ridge include equal protrusions from the outside surface. With some examples, the first ridge and the second ridge may include different protrusions from the outside surface. The first ridge and the second ridge may become haptically discernible. By providing a first ridge and a second ridge of different height, the haptic structure, in particular the first end section and the second end section may become haptically discernible. It is conceivable, that the first ridge, having a larger or smaller height than the second ridge, is located at a left hand side of the haptic track as seen from the first end section to the second end section, whereas the second ridge having a smaller or larger height than the first ridge is located at a right-hand side of the haptic track.

In a further example, the haptic track includes at least a first surface segment, a second surface segment, and a third surface segment. The first surface segment, the second surface segment, and the third surface segments are separated from each other along the haptic track. Each one of the first surface segment, the second surface segment, and the third surface segment are individually coupled to a sensor segment of the touch sensitive sensor arrangement. Typically, the touch sensitive sensor arrangement includes numerous sensor segments that are arranged along and separated along the extension of the haptic tracks. In this way, a sliding motion of an object, e.g., of a finger along the haptic track can be detected in discrete steps by the various sensor segments.

The haptic track includes at least three surface segments. The first surface segment is located at the first end section of the haptic structure. The second surface segment is located at the second end section of the haptic structure and the third surface segment is located somewhere between the first and the second end sections on the haptic track. Typically, the first sensor segment is located at the first surface segment. The second sensor segment is located at the second surface segment and the sensor segment is located at the third surface segment.

In this way, a sliding motion along the haptic track can be detected by the first sensor segment. During the sliding motion, the object, e.g., a finger, passes over the third surface segment and is detected by the third sensor segment. At the end of the sliding motion, the object arrives at the second surface segment and is detected by the second sensor segment. In this way, and by means of at least three surface segments, each of which being provided with a separate sensor segment, a sliding motion of an object along the haptic track can be precisely detected.

In typical examples, the haptic track includes numerous surface segments and the touch sensitive sensor arrangement includes numerous sensor segments that are arranged along the haptic track from the first and section to the second end section thereof. The haptic track may include at least 5, 10, dozens, or even hundreds of surface segments. The touch sensitive sensor arrangement may include at least 5, 10, dozens, or even hundreds of corresponding sensor segments.

According to a further example, the haptic track includes at least a first track segment and a second track segment. The first track segment extends from the first surface segment to the third surface segment. The second track segment extends from the third surface segment to the second surface segment. In this way, the haptic track is divided into at least two track segments that are separated by the above-mentioned surface segment of the haptic track. The portions of the first and/or the second track segments lying between the first, the second and the third surface segments of the haptic track are free of sensor segments of the touch sensitive sensor arrangement. Alternatively, only the portions of the first track segment and the second track segment that are located between the first, the second, and the third surface segments, may be each provided with numerous sensor segments of the touch sensitive sensor arrangement. In either way, not the entire extension but a portion of the haptic track has to be provided with sensor segment of the touch sensitive sensor arrangement. This may help to reduce expenditure and costs for implementing the trigger arrangement.

With a further example, the first track segment, at least in sections, extends along a first orientation. The second track segment, at least in sections, extends along a second orientation. The first orientation extends at a predefined angle with regard to the second orientation. In other words, the haptic track includes a nonlinear extension, a nonlinear shape or nonlinear contour. Such a nonlinear extension, shape or contour is beneficial to avoid an inadvertent sliding of the object along the haptic track. Sliding along the entire haptic track requires at least one change of a sliding direction in accordance to the nonlinear extension, shape or contour of the haptic track. A user being aware and intending to initiate a bolus injection will intentionally follow the change in direction of the haptic track.

Due to the nonlinear extension, shape, or contour of the haptic track, a rather simple operation of the trigger arrangement is provided if the user wishes to intentionally trigger a bolus injection. An inadvertent activation of the trigger arrangement becomes difficult since it is unlikely, that a user inadvertently follows the nonlinear extension, shape, or contour of the haptic track.

According to a further example, the predefined angle between the first orientation and the second orientation is equal to or exceeds 30°, 45°, 60°, 90°, 120°, 135°, 150°, 165° or 180°. In typical configurations, the predefined angle is larger than 90° it may be even larger than 135°. In this way, the object has to conduct a directional change of a sliding motion in order to correctly follow the haptic track on the outside surface of the body. The haptic track may include at least one or several corner sections or at least one or several curved sections located between the first track segment and the second track segment. In a corner section, the direction of the haptic track changes abruptly. In and along a curved section, the direction of the haptic track changes smoothly as the object slides along the track from the first end section of the haptic structure to the second end section of the haptic structure.

Typically, the first track segment and the second track segments are non-overlapping. The entire haptic track may be free of intersections of track segments. By having a non-overlapping haptic track, a rather intuitive and well-defined sliding motion along the haptic track can be provided.

In a further example, the haptic track includes one of a V-shaped, a U-shaped, an S-shaped, a Z-shaped, and a spiral-shaped structure. With these exemplary structures, there can be at least a first track segment and a second track segment that merge into each other along a corner section or along a curved section, and wherein the first track segment and the second track segment have different, namely first and second orientations that are oriented with regard to each other at a predefined angle larger than or equal to 30°. The mentioned examples of shapes of the haptic track are non-limiting. There may be many further geometric shapes of the haptic track featuring first and second track segments oriented along respective first and second orientations that extend at a predefined angle.

According to another example, each one of the sensor segments of the touch sensitive sensor arrangement includes one of a capacitive sensor, a magnetic sensor, an inductive sensor, an optical sensor or a mechanical switch. With these different types of sensors, a proximity or a direct mechanical contact, between the object sliding along the haptic structure and the touch sensitive sensor arrangement can be detected in discrete steps. Typically, all sensor segments of the touch sensitive sensor arrangement are of equal type. For instance, the touch sensitive sensor arrangement may be implemented as a capacitive sensor arrangement, wherein each sensor segment thereof includes a touch sensitive capacitive sensor. An object in close proximity to such a capacitive sensor modifies the electrostatic field around the sensor. Such a modification of the electrostatic field can be electronically detected by the respective capacitive sensor. Such touch sensitive sensor arrangements can be implemented at moderate costs. Respective touch sensitive pads are commercially available for a wide range of applications.

According to another example, the trigger arrangement further includes a controller connected to the touch sensitive sensor arrangement. The controller is configured to detect a sliding motion of an object along the haptic track within a predefined time interval. Typically, the controller is individually connected to each one of the sensor segments of the touch sensitive sensor arrangement. In some embodiments, the touch sensitive sensor arrangement may include a controller on its own. Then, the individual sensor segments are connected to an inbuilt controller of the touch sensitive sensor arrangement and the touch sensitive sensor arrangement is connected to the controller of the trigger arrangement.

The controller is configured to individually detect a touching of each one of the sensor segments of the touch sensitive sensor arrangement. If a predefined number of sensor segments has been touched by the object within a predefined time interval, the controller is configured to interpret this as a sliding motion along the haptic track. In response to such detection, the controller may be configured to initiate or to trigger a bolus injection of the infusion device. In this way, the sliding motion of the object along the haptic track is conducted at a predefined velocity. Otherwise, the sliding motion will not be interpreted as an intentional sliding motion intended for releasing or initiating the bolus injection.

In this way, the controller is at least configured to detect a mechanical contact or a geometrical vicinity between the object and a first end section of the haptic track at a first point of time and to detect a mechanical contact or a geometrical vicinity between the object and a second end section of the haptic track at a second point of time. The sliding motion of the object along the haptic track is recognized when the second point of time and the first point of time at which the first end section and the second end sections are touched are within a predefined time interval. If the time difference between the first point of time at the second point of time is larger than the predefined time interval, interpretation of a sliding motion is dismissed since the motion of the object was too slow.

Another aspect the disclosure relates to a remote control for a drug delivery device, such as an infusion device. The remote-control includes a housing. The remote-control further has an interface to communicate with a corresponding interface of the delivery device. The remote-control further includes a trigger arrangement as described above. The body of the trigger arrangement is part of the housing of the remote-control or the body of the trigger arrangement is connected to the housing of the remote-control. The trigger arrangement may be fully implemented and integrated into the remote-control. The body of the trigger arrangement may coincide with the housing of the remote-control and vice versa.

The controller of the trigger arrangement may be implemented by a controller of the remote-control or that the controller of the trigger arrangement is integrated into a controller of the remote-control. Moreover, the controller of the trigger arrangement and the controller of the remote-control may coincide. A common controller, e.g., the controller of the remote-control may provide the entire functionality of the controller of the trigger arrangement.

In other words, the controller of the remote-control may be connected to the touch sensitive sensor arrangement of the trigger arrangement. The controller of the remote-control may be further configured to analyze signals provided by the touch sensitive sensor arrangement as an object slides along the haptic structure or the haptic track.

The remote-control typically includes a wireless interface in order to communicate with the infusion device. The remote-control may be a portable remote-control that is configured to communicate with the infusion device being attached to the skin of a patient. The remote-control may inter alia include at least one of a display, a touchscreen, and/or various actuation members, such as buttons. The interface is typically configured to communicate with a correspondingly configured interface of the infusion device. By means of the interface, a bolus injection triggered by a user may be released or activated. For releasing and/or initiating a bolus injection a movement of an object, e.g., movement of a finger of a user is sensed by the trigger arrangement, hence when a user slides along the haptic structure on the outside surface of the housing of the remote-control in a well-defined way.

In still another aspect, an infusion device is provided for administering a medicament to a patient. The infusion device includes a housing, a drive mechanism operably connectable to a container containing a medicament. The infusion device further includes a controller configured to control the operation of the drive mechanism for dispensing of a predefined amount of the medicament from the container. Typically, the control is configured to control administering of the medicament to the patient. The infusion device further includes a trigger arrangement as described above, wherein the body of the trigger arrangement is part of the housing or is connected to the housing of the infusion device. Moreover, the trigger arrangement is connected to the controller of the infusion device. In this way, an intentional sliding motion along the haptic structure of the trigger arrangement can be detected by the touch sensitive sensor arrangement of the trigger arrangement. Once a required and predefined sliding motion of the object along the haptic structure of the trigger arrangement has been detected or identified by at least one of the touch sensitive sensor arrangement and the controller, a predefined bolus injection of the infusion device is released or initiated. The touch sensitive sensor arrangement is an electronic sensor arrangement and the controller is an electronic controller.

The trigger arrangement may be fully integrated into the infusion device. The body of the trigger arrangement and hence the trigger arrangement as such can be integrated into the infusion device. The body of the trigger arrangement may coincide with the housing of the infusion device. The housing of the infusion device may form the body of the trigger arrangement. An outside surface of the body of the trigger arrangement may coincide with an outside surface of the housing of the infusion device. By having the haptic structure arranged on the outside surface of the body of the trigger arrangement, the haptic structure is located on the outside surface of the housing of the infusion device. It is hence haptically discernible by a user. It is palpable by a hand or by one or several fingers of a user or patient. In order to release or to initiate a bolus injection, it is not required for the user to establish a visual inspection of the trigger arrangement or of the infusion device. The bolus injection can be simply triggered and released by using one or several fingers and to slide along the haptic structure on the outside surface of the infusion device.

The controller of the trigger arrangement and the controller of the infusion device may coincide. A common electronic controller, e.g., the controller of the infusion device, may provide the entire functionality of the controller of the trigger arrangement. In other words, the controller of the infusion device may be connected to the touch sensitive sensor arrangement of the trigger arrangement. The controller of the infusion device may be further configured to analyze signals provided by the touch sensitive sensor arrangement as an object slides along the haptic structure or the haptic track thereof.

According to a further example, the infusion device includes a container containing the medicament to be dispensed and to be administered to the patient. The container with the medicament is located and arranged inside the housing of the infusion device. The container may be a replaceable container. Hence, the infusion device may be configured as a reusable device. The container may include an elastic bag filled with the medicament. Withdrawal of the medicament from the container may then be conducted by way of a suction pump of the delivery device. In another example, the container includes a cartridge or a carpule having a tubular-shaped barrel filled with the medicament. One end of the barrel, typically, the distal end, is sealed with a seal, which may include a pierceable septum. The other end, e.g., the proximal end, of the barrel is typically sealed with a piston or bung that is displaceable inside the barrel.

The drive mechanism may include a longitudinally displaceable piston rod configured to exert distally directed pressure onto the piston or bung of the cartridge. In this way, a pressure inside the cartridge can be increased so as to expel a predefined amount of the liquid medicament via the distal end section of the cartridge and hence via an injection needle connected to the interior of the barrel in a fluid transferring manner.

An outlet of the cartridge may be in permanent fluid connection with an injection needle via an infusion line. An injection needle may be adhesively attached to the skin of a patient by means of a patch. With other examples, the injection needle may be attached to or may belong to the infusion device. Then, the infusion device may be directly adhesively attached to the skin of the patient. The infusion line extending from the outlet of the cartridge to the injection needle may be located inside the housing of the infusion device.

Another aspect the disclosure further relates to a method of recognizing of a sliding motion of an object along a haptic track of the trigger arrangement. The method includes the steps of providing of a trigger arrangement as described above. In a first step, a mechanical contact or a close proximity the between the object at a first end section of the haptic track is detected at a first point of time. Thereafter and in a second step, a mechanical contact or a close proximity between the object and a second end section of the haptic track is detected at a second point of time.

Thereafter and as the first and the second points of time have been determined, the sliding motion of the object along the haptic track is recognized, when the second point of time at the first point of time within a predefined time interval. Hence, the time interval between the first point of time and the second point of time may not exceed a predefined maximum time interval. For time intervals between the first point of time at the second point of time smaller than the predefined maximum time interval a sliding motion and hence a sliding motion at a predefined velocity from the first end section of the haptic track to the second end section of the haptic track is detected.

In response to the recognizing of a sliding motion of the object along the haptic tracks, the method may trigger various predefined functions of a drug delivery device or of an injection device. If the trigger arrangement is implemented with a remote control, the recognition of a sliding motion may initiate transmitting of a respective command from the remote control to the delivery device, e.g., in order to initiate a bolus injection.

Even though the trigger arrangement is particularly described in connection with an infusion device or with a remote control for an infusion device, it is by no way limited to infusion devices as such. The trigger arrangement may be implemented with all kinds of drug delivery devices, such as injection devices, inhalers or the like. The trigger arrangement may be also implemented with electronically controlled injection devices, such as pen type injection devices.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound includes at least one peptide for the treatment and/or prophylaxis of diabetes mellitus or complications associated with diabetes mellitus such as diabetic retinopathy, wherein in a further embodiment the pharmaceutically active compound includes at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω- carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2, H-(Lys)5-des Pro36, des Pro37 Exendin-4(1-39)-NH2, des Pro36 Exendin-4(1-39), des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39); or des Pro36 [Asp28] Exendin-4(1-39), des Pro36 [IsoAsp28] Exendin-4(1-39), des Pro36 [Met(O) 14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative; or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2; or a pharmaceutically acceptable salt or solvate of any one of the aforementioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure as it is defined by the claims. Further, it is to be noted, that any reference numerals used in the appended claims are not to be construed as limiting the scope of the disclosure.

BRIEF DESCRIPTION OF THE FIGURES

In the following various embodiments of a trigger arrangement and its implementation into an infusion device are described by making reference to the drawings FIG. 1 schematically illustrates an infusion device.

DETAILED DESCRIPTION

Figure 1:
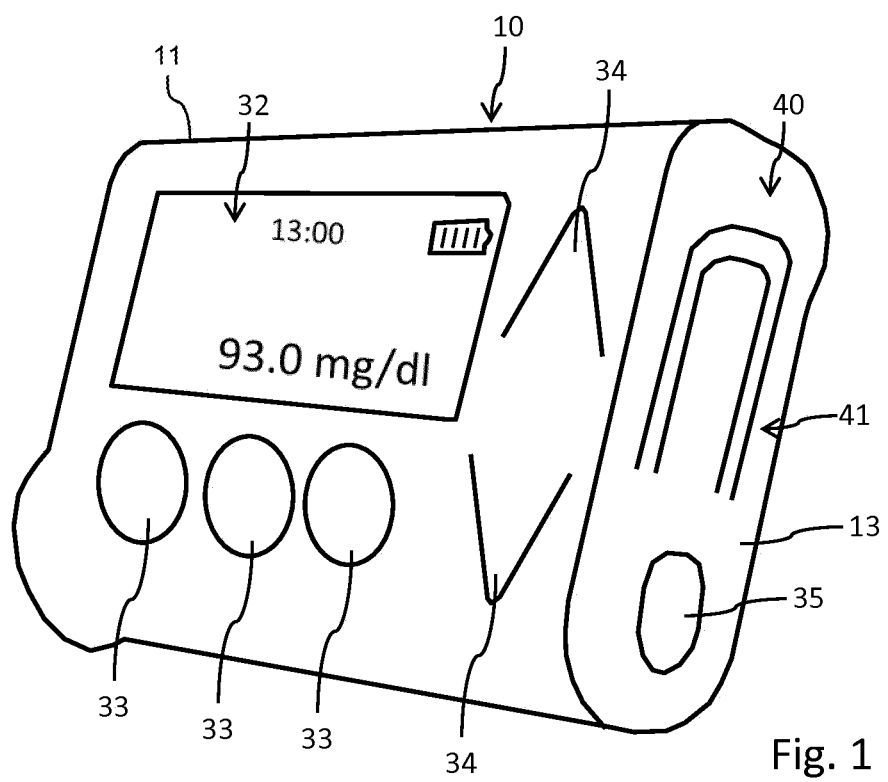

FIG. 1 shows a perspective illustration of an infusion device 10 that may be configured as an insulin pump for treatment of diabetes. The infusion device 10 includes a housing 11. On the outside surface 13 of the housing 11 there are numerous actuation members 33, 34, 35. The actuation members 33, 34, 35 are implemented as buttons. They may be also implemented as switches or knobs. The infusion device 10 further includes a display 32. On the display 32 infusion relevant data is displayed, such as a flow rate of the medicament. The display 32 may further provide other information to the patient, such as the charging state of a battery 25, the actual time, as well as information about a dosing history or information about when a next injection or bolus injection will be due. The display 32 may be implemented as a touchscreen. Then, the infusion device 10 may be void of further actuation members 33, 34, 35.

At least one of the actuation members 35 may be implemented as a sleep button or standby button. By means of the actuation member 35, the entire infusion device may be switched into a sleep mode in order to save energy and to extend the lifetime of the battery 25.

Figure 2:
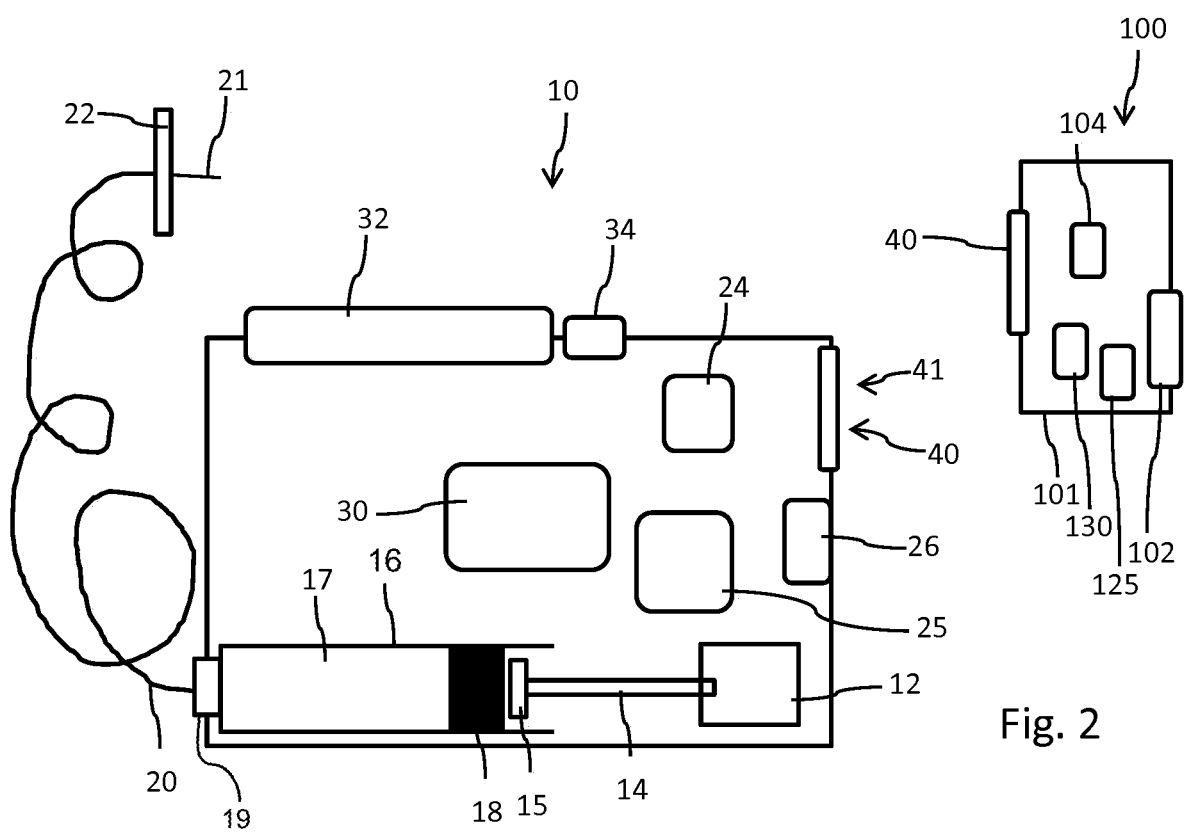
FIG. 2 shows a block diagram of an infusion device together with a corresponding remote control.

In FIG. 2, the internal structure of the infusion device 10 is schematically illustrated. The infusion device 10 includes a controller 30 and a drive mechanism 12. In the illustrated embodiment, the drive mechanism 12 includes an elongated piston rod 14 with a pressure piece 15 at its distal end. The piston rod 14 and hence the drive mechanism 12 is operably engageable with a piston 18 or bung of a container 16, which is presently implemented as a cartridge having a barrel filled with the medicament 17. Near a distal end or outlet 19, the container 16 is sealed, e.g., by means of a pierceable seal, such as a septum. Towards the opposite end, i.e., near the proximal end, the container 16 is sealed by the axially displaceable piston 18. The outlet 19 is connected to an infusion line 20. The end of the infusion line 20 facing away from the outlet 19 of the container 16 is provided with and connected to an injection needle 21. The injection needle 21 is intended to puncture biological tissue. The injection needle 21 protrudes from a patch 22 that is configured and intended to be adhesively attached to the skin of a patient.

With other configurations of the infusion device 10, the needle 21 is directly located inside the housing 11 of the infusion device 10. Then the infusion device 10 itself is configured to be adhesively attached to the skin of a patient. The injection needle 21 may then be deployed to protrude from the outside surface 13 of the housing 11 in order to puncture the skin of the patient.

The electronic controller 30 may be implemented as a microcontroller or as a comparable computing unit. The controller 30 is connected to the display 32 as well as to all actuation members 33, 34, 35. The controller 30 is also connected to the drive mechanism 12. The drive mechanism 12 typically includes an electric drive. Electric energy for powering the controller 30 as well as for activating the drive of the drive mechanism 12 is provided by the battery 25. The battery 25 may include a rechargeable battery. A feedback unit 26 may be provided that is also connected to the controller 30. The feedback unit 26 may be configured to generate an audible or haptic signal so as to indicate to a user, that for instance, a bolus injection has been completed or that a command entered by the user has been accepted or dismissed. The feedback unit 26 may be configured to generate a vibration signal.

The infusion device 10 may be further equipped with an interface 24. The interface 24 is also connected to the controller 30 and is controlled by the controller 30. The interface 24 may be implemented as a wireless transmission interface. The interface 24 may be configured to communicate with a corresponding interface 104 of a remote-control 100. The interfaces 24, 104 may be configured for wireless data transmission according to predefined wireless transmission standards, such as the Wi-Fi standard IEEE 802.11, the NFC standard, an infrared-based communication standard or the Bluetooth communication standard.

The remote-control 100 is optional. The remote-control includes a housing 101 with an outside surface 13. The remote-control 100 includes a controller 130 and at least one or several actuation members connected to the controller 130. Optionally, the remote-control 100 may also include a display 102. The remote-control 100 includes an interface 104 configured for communication with the interface 24 of the infusion device 10.

At least one of the infusion device 10 and the remote-control 100 is equipped with a trigger arrangement 40 that is configured to trigger a bolus injection of the infusion device 10. As indicated in FIG. 1, the trigger arrangement 40 may be located on a dedicated face of the outside surface 13 of the housing 11 of the infusion device 10. Likewise, the trigger arrangement 40 may be provided at an outside surface 13 of the housing 101 of the remote-control 100. The trigger 40 arrangement is now described in more detail in view of FIGS. 3 to 10.

Figure 3:
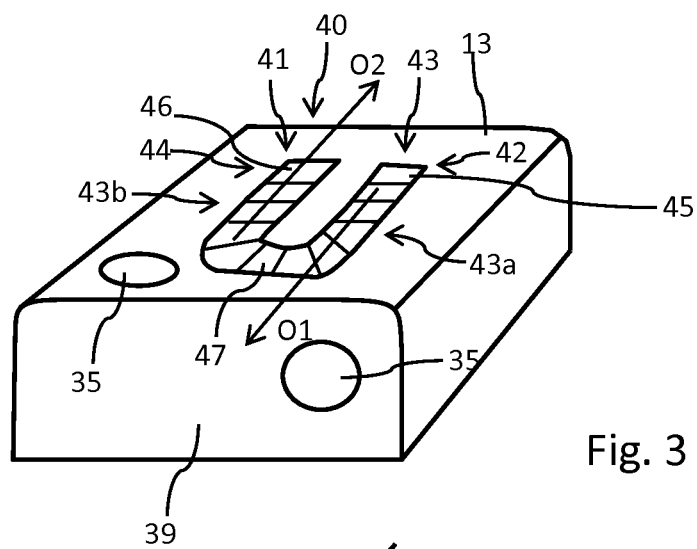
FIG. 3 schematically illustrates an example of a trigger arrangement.

The trigger arrangement 40 as shown in FIG. 3 includes a body 39 with an outside surface 13. Depending on the specific implementation, the body 39 of the trigger arrangement 40 may coincide or may be integrated into one of the housing 11 of the infusion device 10 and the housing 101 of the remote-control 100. When implemented or integrated into the housing 11 of the infusion device 10, the body 39 of the trigger arrangement 40 substantially coincides with the housing 11. The same is valid when the trigger arrangement 40 is implemented in the remote-control 100.

Figure 4:
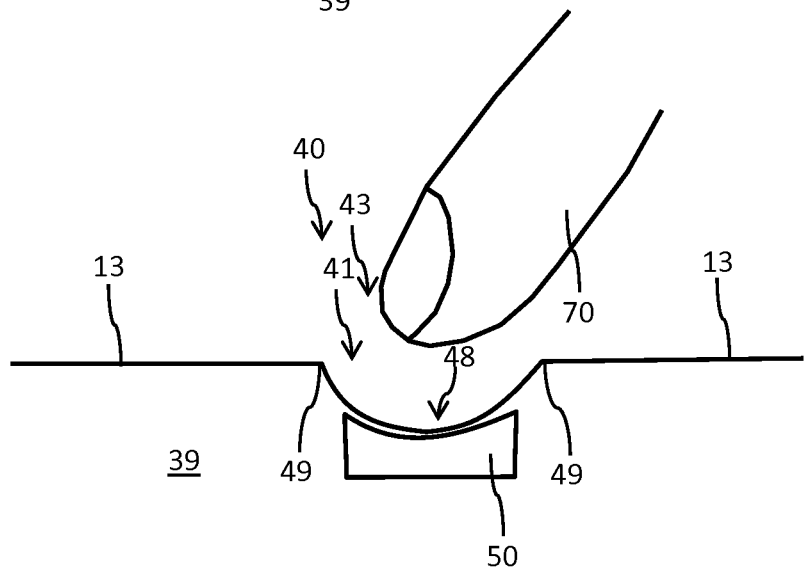
FIG. 4 schematically shows a cross-section through an example of a trigger arrangement.

The trigger arrangement as illustrated in FIGS. 3 and 4 includes a haptic structure 41 arranged on the outside surface 13 of the body 39. The haptic structure 41 includes a first end section 42 and a second end section 44. The haptic structure 41 further includes a haptic track 43 extending from the first end section 42 to the second end section 44. The haptic track 43 continuously extends from the first end section 42 to the second end section 44 without interruption. A touch sensitive sensor arrangement 50 is further provided extending along the haptic track 43 as shown in FIG. 4. The touch sensitive sensor arrangement 50 extends along the haptic track from the first end section 42 to the second end section 44. In this way, the entirety of the haptic track 43 is provided with a touch sensitive sensor arrangement 50. The touch sensitive sensor arrangement 50 is configured to detect a sliding motion of an object 70 along the haptic track, e.g., when the object 70 slides along the haptic track 43 from the first end section 42 to the second end section 44.

As illustrated in FIG. 3, the haptic structure 41 and its haptic track 43 is divided into various surface segments 45, 46, 47. Here, only three surface segments 45, 46, 47 are exemplary illustrated. The first surface segment 45 may coincide with the first end section 42 of the haptic track 43. The second surface segment 46 may coincide with the second end section 44 of the haptic track 43. The third surface segment 47 may be located on the haptic track 43 between the first end section 42 and the second end section 44. The third surface segment 47 is separated from both the first end section 42 and the second end section 44.

The haptic structure 41 is haptically discernible by a user or patient. The haptic structure 41 as illustrated in FIG. 4 includes a deepening 48 in the outside surface 13. The deepening 48 includes a concave shaped groove in the outside surface 13 of the body 39. The groove is complementary shaped to the shape of the object 70 that is intended to slide along the haptic track 43. The groove, and hence the deepening 48, may extend all along the haptic track 43, namely from the first end section 42 to the second end section 44. The deepening 48 may include a constant cross-section or depth along the elongation of the haptic track 43.

With some examples, the deepening 48 may include a varying depth along the haptic track 43. The width of the deepening 48 is somewhat larger than the respective cross-section or width of the object 70 to be placed inside the deepening 48. Hence, the separation between oppositely located edges 49 along which the plane shaped outside surface 13 of the body 39 extends into the deepening 48 is slightly larger than the respective with of the object 70, e.g., a fingertip of a person.

The width and/or the entire cross section of the deepening 48 may be constant along the elongation of the haptic track 43. In some examples, the width and/or the entire cross section of the deepening 48 may vary along the elongation of the haptic track. In this way, the first end section 42 and the second end section 44 become haptically distinguishable.

Figure 10:
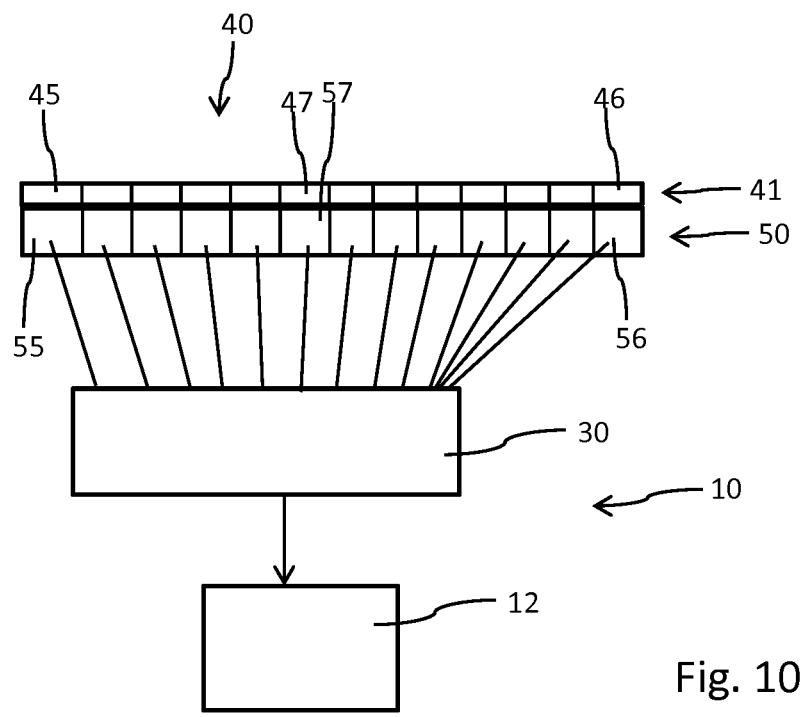
FIG. 10 is a block diagram of the touch sensitive sensor arrangement of the trigger arrangement.

Below the deepening 48, and inside the body 39, the touch sensitive sensor arrangement 50 is provided. As illustrated in FIG. 10, the touch sensitive sensor arrangement 50 may include numerous sensor segments 55, 56, 57. A first sensor segment 55 is located beneath the first end section 42 of the haptic track 43. A second sensor segment 56 is located beneath the second end section 44 of the haptic track 43 and a third sensor segment 57 is located beneath the third surface segment 47 of the haptic track 43.

As illustrated in FIG. 10, each one of the sensor segments 55, 56, 57 is individually connected to the controller 30. Each one of the sensor segments 55, 56, 57 may include a touch sensitive sensor, such as a capacitive sensor, a magnetic sensor, an inductive sensor an optical sensor, or a mechanical switch. In this way, a touch-based sliding of the object 70 along the touch sensitive sensor arrangement 50 can be detected by the controller 30. The controller 30 may be configured to trigger a bolus injection of the infusion device 10 in response to detect a sliding motion of the object 70 along the haptic track 43.

Figure 5:
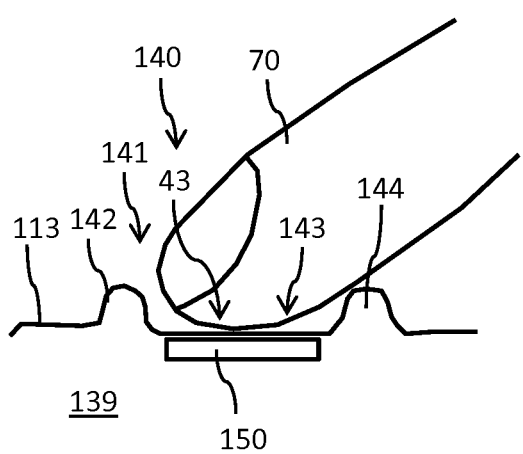
FIG. 5 schematically shows a cross-section through another example of a trigger arrangement.

In the cross-section according to FIG. 5, another example of a haptic structure 141 is illustrated.

Also this haptic structure 141 may include a shape as illustrated in FIG. 3 or as illustrated in any one of the FIGS. 6 to 9. Here and contrary to the example of FIG. 4, the haptic structure 141 and the respective trigger arrangement 140 include two ridges, namely a first ridge 142 and a second ridge 144. The two ridges 142, 144 enclose a haptic track 43 extending along the outside surface 113 of the body 139 of the trigger arrangement 140. Beneath the haptic track 43 a touch sensitive sensor arrangement 150 is also provided extending all along the haptic track 43. The haptic track 43 according to FIG. 5 also includes a first end section 42 and a second end section 44. The two ridges 142, 144 provide a lateral border of the longitudinally extending haptic track 43. An intermediate space 143 between the two ridges 142, 144 is accessible to the object 70 and hence to the finger of a user.

The two ridges 142, 144 and hence the haptic track 43 located between is palpable and hence haptically discernible by the fingers of a patient. Without having visual contact to the trigger arrangement 140 a user may simply palpate the location and the orientation of the trigger arrangement 140 and its haptic structure 141. With a finger the user may then slide along the haptic structure in order to trigger the bolus injection of the infusion device 10. The two ridges 142, 144 extend parallel to each other along the side edges of the haptic track 43. The two ridges 142, 144 may include equal height and may equally protrude from the plane shaped outside surface 113.

The ridges 142, 144 may extend continuously and uninterrupted along the haptic track 43. With other examples, the ridges 142, 144 may be intersected by at least one gap. Moreover, the ridges 142, 144 may include a varying height as they extend from the first end section 42 to the second end section 44 of the haptic structure 141. In this way, the two ridges 142, 144 may become perceptibly distinguishable.

Figure 6:
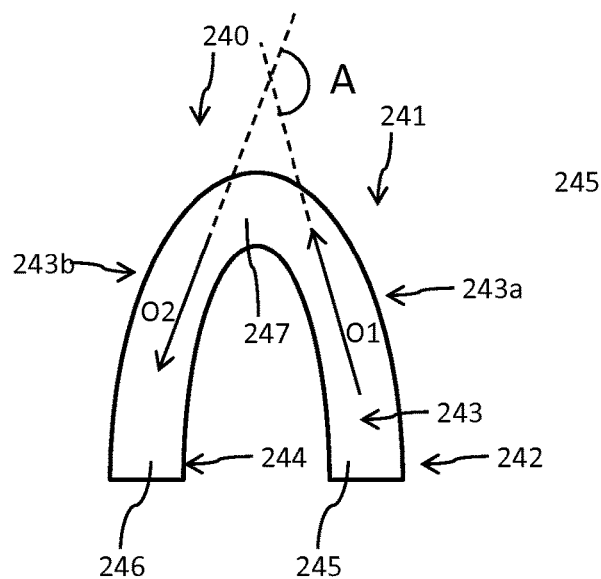
FIG. 6 is a top view of one example of a haptic structure of a trigger arrangement.

As illustrated in FIG. 3 and FIGS. 6 to 9 the haptic structure 41 and its haptic track 43 includes a nonlinear extension on the outside surface 13. The haptic structure 41 as illustrated in FIG. 3 includes a U-shaped structure. The haptic track 43 can be divided at least into a first track segment 43a and a second track segment 43b. The first track segment 43a extends from the first end section 42 and hence from the first surface segment 45 to the third surface segment 47. The second track segment 43b extends from the third surface segment 47 to the second end section 44. The first track segment 43a extends along a first orientation O1 and the second track segment second track segment 43b extends along a second orientation O2. As illustrated in FIG. 6, the first orientation O1 and the second orientation O2 extends at a predefined angle A which exceeds 45°, 60°, 93, 120°, 135°, 150°, 165° or 180°.

In the example of FIG. 3, the first orientation O1 is substantially diametrically opposite to the second orientation O2. The first orientation O1 may be defined by a distance or direction from the first surface segment 45 to the third surface segment 47. The second orientation O2 may be defined by a distance or direction from the third surface segment 47 to the second surface segment 46. By having first and second track segments extending at substantially different orientations, an inadvertent sliding of the object 70 along the entirety of the haptic track 43 can be effectively avoided.

A user can slide along the entire haptic track 43 intentionally since the sliding movement of the object 70 along the haptic track 43 requires a well-defined reorientation of the sliding motion. This can be intentionally achieved when the user enters the haptic structure 41, 141, and hence the deepening 48 or the intermediate space 143 between the ridges 142, with an object 70 and slides along the haptic track 43. In this way, a rather simple and intuitive bolus injection activation can be provided with a maximum safety against inadvertent bolus injection activation.

In FIGS. 6 to 9, further examples of trigger arrangements 240, 340, 440, 544 and infusion device 10 are illustrated. The trigger arrangement 240 according to FIG. 6 includes a haptic structure 241 with a haptic track 243 extending from a first end section 242 to a second end section 244. The haptic structure 241 and the respective haptic track 243 is bow-shaped or arc-shaped. On a crest of the haptic track 243 a third surface segment 247 is located. Near the first end section 242 a first surface segment 245 is provided. Near or coinciding with the second end section 244 a second surface segment 246 is provided. The first track segment 243a extends from the first surface segment 245 to the third surface segment 247. A second track segment 243b extends from the third surface segment 247 to the second surface segment 246. As illustrated, the angle A between the first orientation O1 of the first track segment 243a and the second orientation O2 of the second track segment 243b is larger than 90° or even larger than 120°.

A user or patient intending to trigger a bolus injection has to put their finger onto the first end section 242 of the haptic track 243 and slide along the entire haptic track 243 until their finger reaches the second end section 244. The respective sliding motion is detected by the touch sensitive sensor arrangement 50 located underneath and is further analyzed by the controller 30 so as to trigger a bolus injection of the infusion device 10.

Figure 7:
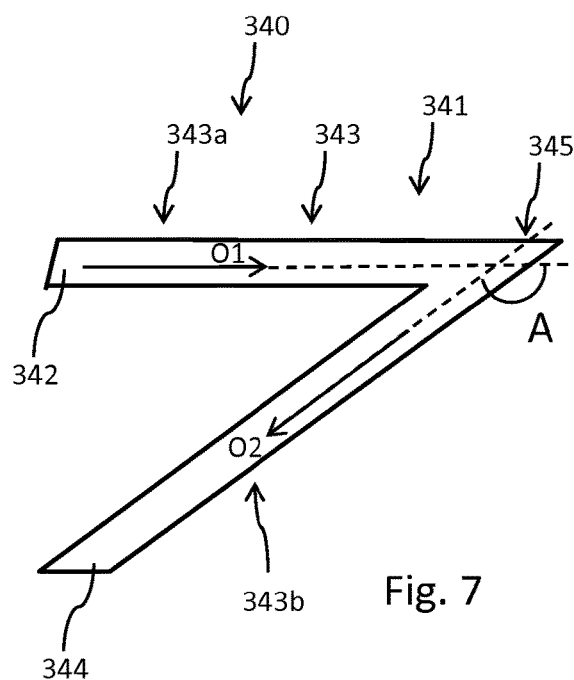
FIG. 7 is a top view of another example of a haptic structure of the trigger arrangement.

With the example of FIG. 7, the trigger arrangement 340 includes a haptic structure 341 with a first end section 342 and a second end section 344. The haptic track 343 continuously extends from the first end section 342 to the second end section 344. The haptic track 343 includes a V-shaped structure. Here, a first track segment 343a and a second track segment 343b each include a straight and elongated shape. The first track segment 343a and the second track segment 343b merge in a corner section 345. Also here, the angle A between a first orientation O1 and a second orientation O2 is larger than 90°, larger than 120° and even larger than 135°.

Figure 8:
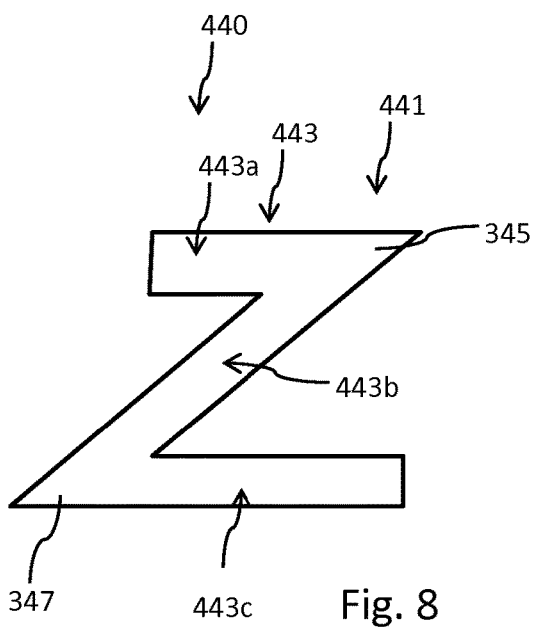
FIG. 8 is a top view of a further example of a haptic structure of the trigger arrangement.

A further example of a haptic structure 441 of another trigger arrangement 440 is shown in FIG. 8. Here, the haptic structure 441 includes a haptic track 443 with three straight shaped track segments 443a, 443b and 443c that are arranged to form a Z-shaped haptic track 443. A first track segment 443a and a third track segment 443c may extend substantially parallel to each other whereas a second track segment 443b interconnects the first track segment 443a and the third track segment 443c. The second track segment 443b extends at a predefined angle with regard to the first track segment 443a and the third track segment 443c. Also here, the angle is larger than 90°, larger than 120° or even larger than 135°. The haptic track 443 includes two corner sections 345 and 347. In each corner section 345, 347 the object 70 sliding along the haptic track 443 has to change a sliding direction in order to correctly follow the haptic track 443.

Figure 9:
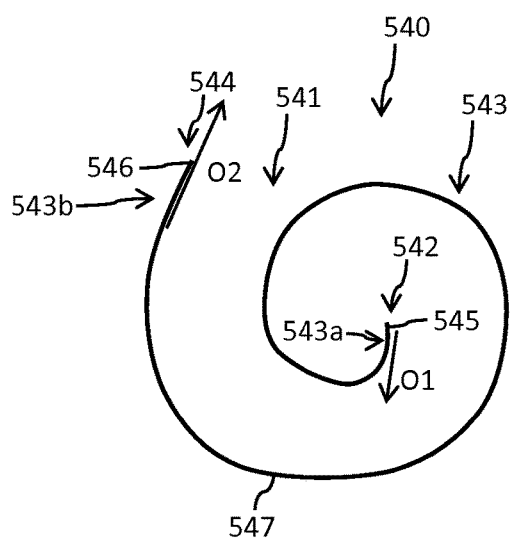
FIG. 9 is a top view of another example of a haptic structure of the trigger arrangement.

In FIG. 9 another trigger arrangement 540 is illustrated with a spiral-shaped haptic structure 541. The spiral-shaped haptic structure 541 includes a first end section 542 and a second end section 544. Here, the first and section 542 is an inner end section and the second end section 544 is an outer end section of the spiral-shaped haptic track 543. At the first end section 542 the haptic track 543 includes a first surface segment 545. At the second end section 544 the haptic track 543 includes a second surface segment 546. Between the first and the second end sections 542, 544 the haptic track 543 includes at least a third surface segment 547. Here, rather short track segment 543*a* with a first orientation O1 in close proximity of the first surface segment 545 can be defined. The first orientation O1 can be considered or defined as a tangent to the haptic track 543 at the first end section 542.

The spiral shaped haptic track 543 further includes a second orientation O2 in close vicinity to the second surface segment 546. Also here, rather short track segment 543*b* with a second orientation O2 in close proximity of the second surface segment 546 can be defined. It is apparent from FIG. 9 that the first orientation O1 and the second orientation O2 are almost diametrically opposite to each other. An angle between the first orientation O1 and the second orientation O2 is at least larger than 165° or substantially equals 180°.

Figure 11:
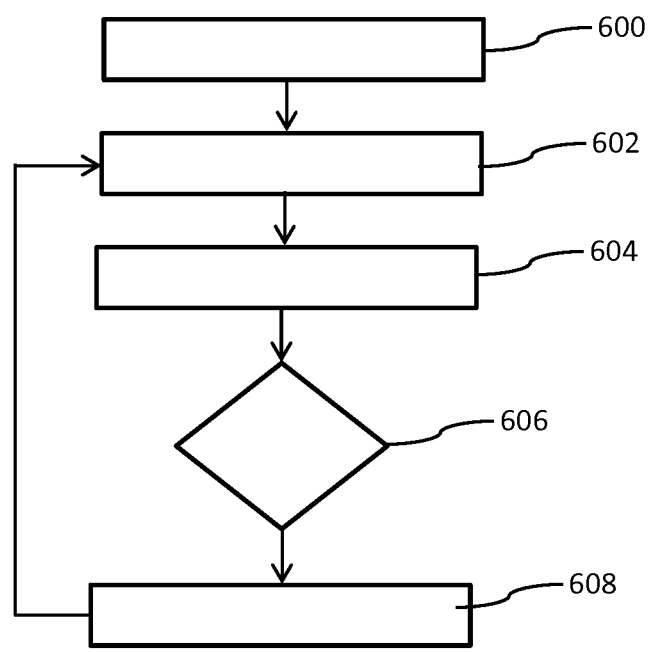
FIG. 11 is a flowchart of a method of recognizing a sliding motion of an object along a haptic track of the trigger arrangement.

In the flowchart according to FIG. 11 the method of recognizing a sliding motion of an object 70 along a haptic track 43 of the trigger arrangement 40 as described above is schematically illustrated. Here, in a first step 600 the trigger arrangement 40 is provided as described above e.g. in connection with FIG. 3. Thereafter in step 602 a mechanical contact or a close proximity between an object 70 and a first end section 42 of the haptic track 43 is detected at a first point of time t1. As the object 70 slides along the haptic track 43 and arrives at the second end section 44 of the haptic track 43, the mechanical contact of the object or close proximity of the object to the second end section 44 is also detected at a second point of time t2 in step 604.

In a subsequent step or concurrently with the detection of the mechanical contact at the second end section in the following step 606 the first point of time t1 and the second point of time are mutually compared. If a time interval between the first point of time t1 and the second point of time t2 is below a predefined threshold the method continues with step 608. There, the occurrence of a detection of a mechanical contact of the object and the haptic track at first and second points of time within a predefined time interval t is interpreted as a sliding motion intended to trigger a bolus injection of the infusion device 10.

In another situation, wherein the time interval between the first point of time t1 and the second point of time t2 exceeds the predefined time interval t, the detection of the object 70 at the first end section 42 and the second end section 44 is dismissed and disregarded. The method then returns to step 602.

The method and a touch detection of the haptic track 43 may be constantly active while the infusion device 10 is in standby or active mode. However, the trigger arrangement 40 may be switched off or deactivated, e.g., by switching the infusion device 10 into a sleep mode. This may save energy and may extend the battery lifetime.

REFERENCE NUMBERS

- 10 infusion device
- 11 housing
- 12 drive mechanism
- 13 outside surface
- 14 piston rod
- 15 pressure piece
- 16 container
- 17 medicament
- 18 piston
- 19 outlet
- 20 infusion line
- 21 needle
- 22 patch
- 24 interface
- 25 battery
- 26 feedback unit
- 30 controller
- 32 display
- 33 actuation member
- 34 actuation member
- 35 actuation member
- 39 body
- 40 trigger arrangement
- 41 haptic structure
- 42 end section
- 43 haptic track
- 43*a* track segment
- 43*b* track segment
- 44 end section
- 45 surface segment
- 46 surface segment
- 47 surface segment
- 48 deepening
- 49 edge
- 50 sensor arrangement
- 55 sensor segment
- 56 sensor segment
- 57 sensor segment
- 70 object
- 100 remote control
- 101 housing
- 102 display
- 104 interface
- 113 outside surface
- 125 battery
- 130 controller
- 139 body
- 140 trigger arrangement
- 141 haptic structure
- 142 ridge
- 143 intermediate space
- 144 ridge
- 150 sensor arrangement
- 240 trigger arrangement
- 241 haptic structure
- 242 end section
- 243 haptic track
- 243*a* track segment
- 243*b* track segment
- 244 end section
- 245 surface segment
- 246 surface segment
- 247 surface segment
- 340 trigger arrangement
- 341 haptic structure
- 342 end section
- 343 haptic track
- 343*a* track segment
- 343*b* track segment
- 344 end section
- 345 corner section
- 440 trigger arrangement
- 441 haptic structure
- 442 end section
- 443 haptic track
- 443*a* track segment 443b track segment
443c track segment
445 corner section
447 corner section
540 trigger arrangement
541 haptic structure
542 end section
543 haptic track
543 track segment
543 track segment
544 end section
545 surface segment
546 surface segment
547 surface segment

The invention claimed is:

1. A trigger arrangement for an infusion device, the trigger arrangement being configured to trigger a bolus injection of the infusion device and comprising:
a body having an outside surface,
a haptic structure arranged on the outside surface or integrated into the outside surface, wherein the haptic structure comprises a first end section and a second end section, and wherein the haptic structure comprises a haptic and palpable track extending from the first end section to the second end section and terminating at the first end section and at the second end section, respectively,
a touch sensitive sensor arrangement extending along the haptic and palpable track and configured to detect a sliding motion of an object along the haptic and palpable track, and
an electronic controller connected to the touch sensitive sensor arrangement and connectable to a drive mechanism of the infusion device, wherein the electronic controller is operable to trigger the bolus injection when a predefined sliding pattern of the object along the haptic and palpable track is detected by the touch sensitive sensor arrangement,
wherein the haptic and palpable track comprises a first track segment and a second track segment, the first track segment extends from the first end section to a surface segment, and the second track segment extends from the second end to the surface segment, and
wherein the first track segment at least in sections extends along a first orientation, the second track segment at least in sections extends along a second orientation, and the first orientation extends at a predefined angle with regard to the second orientation.

2. The trigger arrangement according to claim 1, wherein the haptic structure comprises a recess in the outside surface.

3. The trigger arrangement according to claim 1, wherein the haptic structure comprises at least a first ridge protruding from the outside surface.

4. The trigger arrangement according to claim 3, wherein the haptic structure comprises at least a second ridge protruding from the outside surface, the second ridge extends parallel to the first ridge, and the haptic and palpable track is located or extends between the first ridge and the second ridge.

5. The trigger arrangement according to claim 1, wherein the surface segment is a first surface segment, the haptic and palpable track comprises at least a second surface segment and a third surface segment, the first surface segment, the second surface segment, and the third surface segment are separated from each other along the haptic and palpable track, and each one of the first surface segment, the second surface segment, and the third surface segment are individually coupled to sensor segments of the touch sensitive sensor arrangement.

6. The trigger arrangement according to claim 5, wherein each one of the sensor segments of the touch sensitive sensor arrangement comprises one of a capacitive sensor, a magnetic sensor, an inductive sensor, an optical sensor, or a mechanical switch.

7. The trigger arrangement according to claim 5, wherein the first track segment extends from the first surface segment to the third surface segment and wherein the second track segment extends from the third surface segment to the second surface segment.

8. The trigger arrangement according to claim 7, wherein the predefined angle between the first orientation and the second orientation is greater than or equal to 45°.

9. The trigger arrangement according to claim 1, wherein the haptic and palpable track comprises one of a V-shaped, a U-shaped, an S-shaped, a Z-shaped, and a spiral-shaped structure.

10. The trigger arrangement according to claim 1, wherein the electronic controller is configured to detect the sliding motion of the object along the haptic and palpable track within a predefined time interval.

11. A method comprising:
detecting a mechanical contact or a close proximity between the object of claim 1 and the first end section of the haptic and palpable track of the trigger arrangement of claim 1 at a first point in time,
detecting a mechanical contact or a close proximity between the object and the second end section of the haptic and palpable track at a second point in time, and
recognizing the sliding motion of the object along the haptic and palpable track between the first end section and the second end section when the second point in time and the first point in time are within a predefined time interval.

12. The method of claim 11, further comprising expelling a medicament from a cartridge of an infusion device comprising the trigger arrangement when the second point in time and the first point in time are recognized to be within the predefined time interval.

13. The method of claim 11, further comprising vibrating an infusion device comprising the trigger arrangement, by a feedback unit, when the second point in time and the first point in time are recognized to be within the predefined time interval.

14. The method of claim 11, further comprising generating an audible or haptic signal, by a feedback unit, when the second point in time and the first point in time are recognized to be within the predefined time interval.

15. The method of claim 11, further comprising detecting a mechanical contact or a close proximity between the object and a third section of the haptic and palpable track at a third point in time, the third section located between the first end section and the second end section.

16. The method of claim 15, wherein recognizing the sliding motion of the object along the haptic and palpable track between the first end section and the second end section uses contact information from the third section of the haptic and palpable track.

17. The trigger arrangement according to claim 1, wherein the first orientation is different from the second orientation.

18. An infusion device for administering a medicament to a patient, the infusion device comprising:
a housing, a drive mechanism operably connectable to a container containing a medicament, an electronic controller configured to control operation of the drive mechanism for dispensing of a predefined amount of the medicament from the container, a trigger arrangement configured to trigger a bolus injection of the infusion device, the trigger arrangement comprising:

a body having an outside surface, a haptic structure arranged on the outside surface or integrated into the outside surface, wherein the haptic structure comprises a first end section and a second end section, and wherein the haptic structure comprises a haptic and palpable track extending from the first end section to the second end section and terminating at the first end section and at the second end section, respectively, and a touch sensitive sensor arrangement extending along the haptic and palpable track and configured to detect a sliding motion of an object along the haptic and palpable track, wherein the body of the trigger arrangement is part of the housing or is connected to the housing and wherein the trigger arrangement is connected to the electronic controller, and wherein the electronic controller is connected to the touch sensitive sensor arrangement and connectable to the drive mechanism, wherein the electronic controller is operable to trigger the bolus injection when a predefined sliding pattern of the object along the haptic and palpable track is detected by the touch sensitive sensor arrangement, wherein the haptic and palpable track comprises a first track segment and a second track segment, the first track segment extends from the first end section to a surface segment, and the second track segment extends from the second end to the surface segment, and wherein the first track segment at least in sections extends along a first orientation, the second track segment at least in sections extends along a second orientation, and the first orientation extends at a predefined angle with regard to the second orientation.

19. The infusion device according to claim 18 further comprising a container containing the medicament and being arranged inside the housing.

* * * * *

UNITED STATES PATENT AND TRADEMARK OFFICE
CERTIFICATE OF CORRECTION

| | |
|---|---|
| PATENT NO. | : 11,596,734 B2 |
| APPLICATION NO. | : 16/652161 |
| DATED | : March 7, 2023 |
| INVENTOR(S) | : Christian Rehbein |

It is certified that error appears in the above-identified patent and that said Letters Patent is hereby corrected as shown below:

In the Claims

Column 21, Line 44, Claim 1, after "end", insert -- section --

Signed and Sealed this
Eighteenth Day of April, 2023

*Katherine Kelly Vidal*

Katherine Kelly Vidal
*Director of the United States Patent and Trademark Office*